United States Patent [19]

Pascual

[11] Patent Number: 5,130,331
[45] Date of Patent: Jul. 14, 1992

[54] THIENYLTHIOUREAS, -ISOTHIOUREAS AND -CARBODIIMIDES

[75] Inventor: Alfons Pascual, Basel, Switzerland

[73] Assignee: Ciba-Geigy Corporation, Ardsley, N.Y.

[21] Appl. No.: 594,883

[22] Filed: Oct. 9, 1990

[30] Foreign Application Priority Data

Oct. 13, 1989 [CH] Switzerland .................. 3750/89

[51] Int. Cl.$^5$ ............... A61K 31/38; C07D 333/36
[52] U.S. Cl. .................................. 514/447; 549/68; 549/69
[58] Field of Search ................ 549/69, 68; 514/447

[56] References Cited

U.S. PATENT DOCUMENTS

4,194,008 3/1980 Enders et al. .................. 424/322
4,240,820 12/1980 Dickore et al. ................. 549/69

FOREIGN PATENT DOCUMENTS

300972 1/1989 European Pat. Off. ............. 549/69
2657772 6/1978 Fed. Rep. of Germany .
2727416 1/1979 Fed. Rep. of Germany .
2727529 1/1979 Fed. Rep. of Germany .

OTHER PUBLICATIONS

W. McCarthy et al., *J. Org. Chem.*, "Heterocyclic amines," 42(9), pp. 1508–1510 (1977).
E. Brunett et al., *J. Heterocycl. Chem.*, "Heterocyclic amines," 10(6), pp. 1067–1068 (1973).

*Primary Examiner*—Richard L. Raymond
*Assistant Examiner*—Mack W. Russell
*Attorney, Agent, or Firm*—Kevin T. Mansfield; Edward McC. Roberts

[57] ABSTRACT

The novel substituted 3-thienylthioureas, -isothioureas and -carbodiimides of formula I

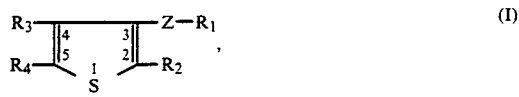

in which $R_1$ is $C_1$–$C_{12}$alkyl, $C_1$–$C_4$alkyl substituted by a $C_3$–$C_6$cycloalkyl radical, $C_3$–$C_8$cycloalkyl, or $C_3$–$C_6$cycloalkyl substituted by a $C_1$–$C_4$alkyl radical; $R_2$, $R_3$ and $R_4$ are each, independently of the others, hydrogen, $C_1$–$C_6$alkyl, phenyl, or phenyl substituted by from 1 to 3 radicals from the group halogen, $C_1$–$C_6$alkyl, $C_1$–$C_4$alkoxy and $C_1$–$C_6$haloalkyl having from 1 to 9 halogen atoms; Z is a group —NH—CS—NH—, —N=C(SR$_5$)—NH— or —N=C=N—; and $R_5$ is $C_1$–$C_6$alkyl or $C_3$–$C_5$ alkenyl; with the proviso that at least one of the radicals $R_2$, $R_3$ and $R_4$ is other than hydrogen; and the salts of compounds of formula I in which Z is the group —N=C(SR$_5$)—NH—, have valuable pesticidal properties. Compositions containing those compounds, processes for the preparation thereof and their use as pesticides, especially as insecticides and acaricides in agriculture, are described.

18 Claims, No Drawings

THIENYLTHIOUREAS, -ISOTHIOUREAS AND -CARBODIIMIDES

The present invention relates to novel substituted 3-thienylthioureas, -isothioureas and -carbodiimides, salts of those compounds with organic and inorganic acids, processes and intermediates for their preparation, pesticidal compositions containing those compounds, and their use in controlling pests.

According to the invention, compounds of formula I are proposed

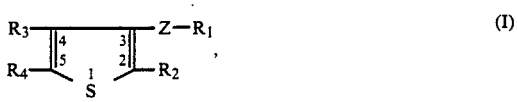
(I)

in which $R_1$ is $C_1$-$C_{12}$alkyl, $C_1$-$C_4$alkyl substituted by a $C_3$-$C_6$cycloalkyl radical, $C_3$-$C_8$cycloalkyl, or $C_3$-$C_6$cycloalkyl substituted by a $C_1$-$C_4$alkyl radical; $R_2$, $R_3$ and $R_4$ are each, independently of the others, hydrogen, $C_1$-$C_6$alkyl, phenyl, or phenyl substituted by from 1 to 3 radicals from the group halogen, $C_1$-$C_6$alkyl, $C_1$-$C_4$alkoxy and $C_1$-$C_6$haloalkyl having from 1 to 9 halogen atoms; Z is a group —NH—CS—NH—, —N=C(SR$_5$)—NH— or —N=C=N—; and $R_5$ is $C_1$-$C_6$alkyl or $C_3$-$C_5$alkenyl; with the proviso that at least one of the radicals $R_2$, $R_3$ and $R_4$ is other than hydrogen; and the salts of compounds of formula I in which Z is the group —N=C(SR$_5$)—NH—.

Halogen atoms that come into consideration as substituents are either fluorine and chlorine or bromine and iodine, fluorine and chlorine being preferred.

The alkyl radicals that come into consideration also as substituents of other groups may be straight-chain or branched. Methyl, ethyl, propyl, i-propyl, butyl, i-butyl, sec.-butyl, tert.-butyl or pentyl, hexyl, octyl etc. and the isomers thereof may be mentioned as examples of such alkyl radicals.

The alkenyl radicals that come into consideration as substituents may be straight-chain or branched and contain one or more double bonds. Examples of such alkenyl radicals are, inter alia, allyl, 1-propenyl, isopropenyl, allenyl, butenyls and pentenyls.

The $C_1$-$C_6$alkyl radicals mono- or poly-substituted by halogen that come into consideration as substituents within the scope of the definition according to the invention may be straight-chain or branched and only partially halogenated or also perhalogenated, the above definitions applying for the halogen atoms. Suitable examples of such substituents are, inter alia, methyl mono- to tri-substituted by fluorine, chlorine and/or bromine, such as, for example, $CHF_2$ or $CF_3$; ethyl mono-to penta-substituted by fluorine, chlorine and/or bromine, such as, for example, $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or i-propyl mono- to hepta-substituted by fluorine, chlorine and/or bromine, such as, for example, $CH_2CHBrCH_2Br$, $CF_2CHFCF_3$, $CH_2CF_2CF_3$ or $CH(CF_3)_2$; butyl or an isomer thereof mono- to nona-substituted by fluorine, chlorine and/or bromine, such as, for example, $CF(CF_3)CHFCF_3$ or $CH_2(CF_2)_2CF_3$.

The cycloalkyl radicals that come into consideration as substituents are, for example, cyclopropyl, cyclobutyl, cyclopentyl, cyclohexyl and cyclooctyl. Within the scope of the definition according to the invention, the cycloalkyl radicals may be mono- or poly-substituted by a $C_1$-$C_4$alkyl radical and/or bonded by a $C_1$-$C_4$alkylene bridge to the remainder of the molecule.

The compounds of formula I in which Z is —N=C(SR$_5$)—NH—, i.e. the isothioureas of formula I, may also be in the form of their acid addition salts. Both organic and inorganic acids are suitable for the formation of such salts. Examples of such acids are, inter alia, hydrochloric acid, hydrobromic acid, hydriodic acid, nitric acid, various phosphoric acids, sulfuric acid, formic acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid, phenylsulfonic acids or salicyclic acid, preferably oxalic acid.

Compounds of formula I in which Z is —N=C(SR$_5$)—NH— may be in the tautomeric forms corresponding to the structures —N=C(SR$_5$)—NH—⇌—NH—C(SR$_5$)=N—. The invention includes both the individual tautomers and tautomeric mixtures.

The compounds of formula I, wherein at least two of the radicals $R_2$, $R_3$ and $R_4$ are other than hydrogen are of particular importance owing to their biological activity.

Furthermore, those compounds of formula I in which $R_4$ is hydrogen and those in which $R_1$ is $C_1$-$C_4$alkyl or $C_3$-$C_5$cycloalkyl, specifically $C_4H_9(t)$ or $C_3H_7(i)$, are preferred.

Those compounds of formula I in which $R_2$ and $R_3$ are each, independently of the other, $C_2$-$C_5$alkyl, those in which $R_2$ and/or $R_3$ are $C_3H_7(i)$ and those in which $R_5$ is methyl or ethyl are of particular importance.

The compounds of formula I according to the invention can be prepared by processes known per se (cf., for example, EP Patent Application 0 304 025), e.g.:

(a) for the preparation of a compound of formula I in which Z is —NH—CS—NH—, reacting a compound of formula II

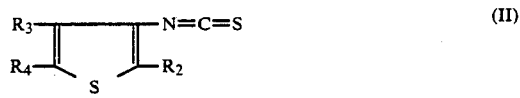
(II)

with a compound of formula III $H_2N$—$R_1$   (III);

or (b) if desired, for the preparation of a compound of formula I in which Z is —N=C(SR$_5$)—NH—, reacting the obtained compound of formula I in which Z is —NH—CS—NH— with a compound of formula IV

X—$R_1$   (IV);

and, if desired, converting an obtained compound of formula I in which Z is —N=C(SR$_5$)—NH— into one of its salts in a manner known per se; or (c) if desired, for the preparation of a compound of formula I in which Z is —N=C=N—, removing hydrogen sulfide from a resulting compound of formula I in which Z is —NH—CS—NH—; $R_1$ to $R_5$ in formulae II to IV being as defined above and X being a leaving group.

Process (a) is usually carried out under normal pressure and in the presence of an organic solvent or diluent. The temperature is from 0° to +150° C., preferably from +10° to 70° C. Suitable solvents or diluents are, for example, ethers and ethereal compounds, such as diethyl ether, diisopropyl ether, dibutyl ether, dioxane, dimethoxyethane or tetrahydrofuran; N,N-dialkylated carboxylic acid amides; aliphatic, aromatic and halogenated hydrocarbons, such as benzene, toluene, xylenes, chloroform, methylene chloride, carbon tetrachloride or chlorobenzene; nitriles, such as acetonitrile or propionitrile; and ketones, such as acetone, methyl ethyl ketone, methyl isopropyl ketone, methyl isobutyl ketone or cyclohexanone.

Process (b) is advantageously carried out in an inert organic solvent and under slightly elevated or normal pressure. The temperature is from +10° to 250° C., but is preferably the boiling temperature of the solvent used or from +50° to 150° C. Suitable solvents or diluents are, for example, ethers or ethereal compounds, such as diethyl ether, diisopropyl ether, dioxane or tetrahydrofuran; aromatic hydrocarbons, such as benzene, toluene or xylenes; ketones, such as acetone, methyl ethyl ketone or cyclohexanone, alcohols or dimethylformamide. The reaction is either carried out in the presence of a base, or the salt that may be formed is subjected to subsequent treatment with a base (cf. J. B. Hendricksen et al., "Organic Chemistry", McGraw Hill Book Co., 1970, pp. 378–382).

Suitable leaving groups in starting compounds of formula IV are, for example, halogen atoms, especially chlorine, bromine or iodine, or unsubstituted, halogenated or alkylated sulfonic acid esters, such as, for example, tosylate, brosylate or mono- or di-alkylsulfate (mesylate, dimethyl sulfate).

Process (c) is advantageously carried out under normal pressure in an aprotic organic solvent or diluent. The temperature is from 0° to +150° C., preferably from +10° to 50° C. Suitable solvents or diluents are, for example, ethers and ethereal compounds, such as diethyl ether, diisopropyl ether, dibutyl ether, dioxane, dimethoxyethane or tetrahydrofuran; N,N-dialkylated carboxylic acid amides; aliphatic, aromatic and halogenated hydrocarbons, such as benzene, toluene, xylenes, chloroform, methylene chloride, carbon tetrachloride or chlorobenzene; nitriles, such as acetonitrile or propionitrile; and ketones, such as acetone, methyl ethyl ketone, methyl isopropyl ketone or cyclohexanone. The hydrogen sulfide is removed according to procedures described in the literature (T. Shibanuma, Chemistry Letters 1977, pp. 575–576; S. Kim, Tetrahedron Letters 1985, pp. 1661–1664; W. Weith, B. 6, 1873, p. 1398; G. Amiard, Bull. Soc. Chim. 1956, p. 1360). The reagents used for the removal are, for example, HgO, certain pyridinium salts, chloroacetic acid esters, cyanuric acid chloride, p-toluenesulfochloride or certain phosphoric acid ester derivatives.

The isothiocyanates of formula II used as starting materials are novel. They can be prepared according to methods that are known per se, for example by reacting an aniline of formula V

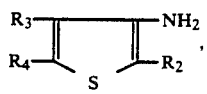　(V)

in which $R_2$, $R_3$ and $R_4$ are as defined above for formula I, with thiophosgene (cf. Helv. Chem. Acta 66, 148; EP Patent Application 043 054).

The process for the preparation of the above compounds of formula II is advantageously carried out in the presence of an organic or inorganic base and a solvent or diluent that is inert with respect to the reactants, at a temperature of from 0° to +100° C. and at normal pressure. Suitable solvents and diluents are, inter alia, ethers or ethereal compounds, such as, for example, diethyl ether, diisopropyl ether, dioxane or tetrahydrofuran; aromatic hydrocarbons, such as benzene, toluene or xylenes; ketones, such as acetone, methyl ethyl ketone or cyclohexanone; or chlorinated hydrocarbons, such as dichloromethane or tetrachloromethane. Suitable bases may be of organic or inorganic origin, such as, for example, sodium hydride, sodium or calcium carbonate, tertiary amines, such as triethylamine, triethylenediamine or 4-dimethylaminopyridine or pyridine.

The aforementioned anilines of formula V are known or can be prepared by methods known per se by, for example, aromatising a corresponding oxime (cf. Synthesis 1977, 200) thereby converting the oxime group into an amino group (cf. JP Patent publication 69-12.895; J. Org. Chem. 1953, 138; Arch. Pharm. 314,557).

The starting compounds of formulae III and IV are for the most part known and can be prepared by methods that are known in principle.

It is already known from German Offenlegungsschriften Nos. 2657772, 2727416 and 2727529 that substituted N-phenyl-N'-alkyl- and -N'-cycloalkyl-thioureas have acaricidal and/or insecticidal activity. EP Patent Application No. 0 300 972 also includes insecticidally and acaricidally active substituted N-thienyl-N'-benzoylureas and -thioureas, with N-[4-methyl-5-(4-chlorophenyl)-thien-3-yl]-N'-(2,6-difluorobenzoyl)thiourea being mentioned specifically. The compounds of formula I according to the invention differ structurally from those compounds essentially by the simultaneous presence of an N-thien-3-yl and an N'-alkyl grouping, and further by the lack of an N'-benzoyl grouping.

Surprisingly, it has now been found that the compounds of formula I of the invention are valuable active ingredients in the control of pests while being well tolerated by warm-blooded animals, fish and plants. In particular, the use of the active ingredients of the invention is directed to insects and arachnids that occur in useful plants and ornamentals in agriculture, especially in cotton, vegetable and fruit plantations, in forestry, in stock and material protection and also in the hygiene sector, especially in connection with domestic animals and productive livestock. The compounds of formula I are especially suitable for the control of plant-destructive sucking insects and spider mites and pests that occur in the soil, such as, for example, Diabrotica balteata. They are effective against all or individual stages of development of normally sensitive species and also resistant species. Their effect may manifest itself in a direct kill of the pests, or not until some time has elapsed, for example during shedding, or may manifest itself in a reduced oviposition and/or hatching rate. The following are included among the above-mentioned pests: of the order Lepidoptera, for example

*Acleris spp., Adoxophyes spp., Aegeria spp., Agrotis spp., Alabama argillaceae, Amylois spp., Anticarsia gemmatalis, Archips spp., Argyrotaenia spp., Autographa spp., Busseola fusca, Cadra cautella, Carposina nipponensis,*

*Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synathedon* spp., *Thaumetopoea* spp., *Tortrix* spp., *Trichoplusia ni* and *Yponomeuta* spp.;

of the order Coleoptera, for example

*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.; of the order Orthoptera, for example *Blatta* spp., *Blattella* spp., *Gryllotalpa* spp., *Leucophaea maderae, Locusta* spp., *Periplaneta* spp. and *Schistocerca* spp.;

of the order Isoptera, for example

*Reticulitermes* spp.; of the order Psocoptera, for example *Liposcelis* spp.; of the order Anoplura, for example *Haematopinus* spp., *Linognathus* spp., *Pediculus* spp., *Pemphigus* spp. and *Phylloxera* spp.; of the order Mallophaga, for example *Damalinea* spp. and *Trichodectes* spp.;

of the order Thysanoptera, for example

*Frankliniella* spp., *Hercinothrips* spp., *Taeniothrips* spp., *Thrips palmi, Thrips tabaci* and *Scirtothrips aurantii;* of the order Heteroptera, for example

*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;

of the order Homoptera, for example

*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;* of the order Hymenoptera, for example

*Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;

of the order Diptera, for example

*Aedes* spp., *Antherigona soccata, Bibio hortulanus, Caliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;

of the order Siphonaptera, for example

*Ceratophyllus* spp., *Xenopsylla cheopis,* of the order Acarina, for example

*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.; and of the order Thysanura, for example

*Lepisma saccharina.*

The mentioned good pesticidal activity of the compounds of formula I of the invention corresponds to a killing rate (mortality) of at least 50–60% of the mentioned pests.

The activity of the compounds of the invention and of the compositions containing them can be substantially broadened and adapted to the prevailing circumstances by the addition of other insecticides and/or acaricides. Examples of suitable additives are representatives of the following classes of active substance: organophosphorus compounds, nitrophenols and derivatives thereof, formamidines, ureas, carbamates, pyrethroids, chlorinated hydrocarbons and Bacillus thuringiensis preparations.

The compounds of formula I are used in unmodified form or, preferably, together with the adjuvants conventionally employed in the art of formulation, and can therefore be formulated in known manner e.g. into emulsifiable concentrates, directly sprayable or dilutable solutions, dilute emulsions, wettable powders, soluble powders, dusts, granulates, and also encapsulations in polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations of those compounds with other insecticides or acaricides and, if desired, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are calcite or sand. In addition, a great number of granulated materials of inorganic or organic nature can be used, e.g. especially dolomite or pulverised plant residues.

Depending on the nature of the compound of formula I to be formulated or of the combinations of those compounds with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tall oil. Mention may also be made of fatty acid methyltaurin salts and modified and unmodified phospholipids as surfactants.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14-moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyl-di-(2-chloroethyl)-ethylammonium bromide.

The surfactants customarily used in the art of formulation are described, for example, in the following publications:

"1985 International Mc Cutcheon's Emulsifiers & Detergents", Glen Rock N.J. USA, 1985", H. Stache, "Tensid-Taschenbuch", 2nd edition, C. Hanser Verlag Munich, Vienna 1981, M. and J. Ash "Encyclopedia of Surfactants", vol. I–III, Chemical Publishing Co., New York, 1980–1981.

The pesticidal compositions according to the invention usually contain 0.1 to 99%, especially 0.1 to 95%, of a compound of formula I or combinations of that compound with other insecticides or acaricides, 1 to 99.9% of a solid or liquid adjuvant and 0 to 25%, preferably 0.1 to 20%, of a surfactant. Whereas commercial products will preferably be formulated as concentrates, the end user will normally employ dilute formulations that contain substantially lower concentrations of active ingredient. Typical concentrations are from 0.1 to 1000 ppm, preferably from 0.1 to 500 ppm. The rate of application per hectare is generally from 1 to 1000 g of active ingredient per hectare, preferably from 25 to 500 g/ha.

Preferred formulations according to the invention are composed especially as follows: (throughout percentages are by weight)

| Emulsifiable concentrates | | | |
|---|---|---|---|
| active ingredient: | 1 to 20%, | preferably | 5 to 10% |
| surfactant: | 5 to 30%, | preferably | 10 to 20% |
| liquid carrier: | 50 to 94%, | preferably | 70 to 85% |
| Dusts | | | |
| active ingredient: | 0.1 to 10%, | preferably | 0.1 to 1% |
| solid carrier: | 99.9 to 90%, | preferably | 99.9 to 99% |
| Suspension concentrates | | | |
| active ingredient: | 5 to 75%, | preferably | 10 to 50% |
| water: | 94 to 24%, | preferably | 88 to 30% |
| surfactant: | 1 to 40%, | preferably | 2 to 30% |
| Wettable powders | | | |
| active ingredient: | 0.5 to 90%, | preferably | 1 to 80% |
| surfactant: | 0.5 to 20%, | preferably | 1 to 15% |
| solid carrier: | 5 to 95%, | preferably | 15 to 90% |
| Granulates | | | |
| active ingredient: | 0.5 to 30%, | preferably | 3 to 15% |
| solid carrier: | 99.5 to 70%, | preferably | 97 to 85% |

The compositions of the invention may also contain further auxiliaries such as stabilisers, antifoams, preservatives, viscosity regulators, binders, tackifiers as well as fertilisers or other active ingredients for obtaining special effects.

The following Examples serve to illustrate the invention but do not limit the invention.

EXAMPLE 1

Preparation of 2,4-diisopropyl-3-thienylisothiocyanate (starting compound)

With stirring, 5.60 g of 2,4-diisopropylthienyl-3-amine hydrochloride are added in small portions, at from 0° to 5° C., to a mixture of 5.50 g of calcium carbonate, 40 ml of water, 3.75 g of thiophosgene, 70 ml of dichloromethane and 2.70 g of sodium hydrogen carbonate. The reaction mixture is stirred at room temperature for 3 hours and then filtered over diatomaceous earth. The organic phase is separated off, washed with 50 ml of saturated NaCl solution and 50 ml of water, dried over magnesium sulfate and then concentrated by evaporation. The title compound of formula

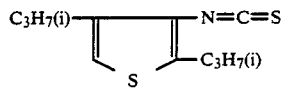

is obtained in the form of a strongly coloured oil, which is used further without being purified.

The thienyl-3-isocyanates of formula II listed in the following are prepared in an analogous manner from the thienyl-3-amines indicated:

$$R_3\text{-}\underset{S}{\overset{}{\text{thienyl}}}\text{-}NH_2,\ R_4,\ R_2$$

| $R_2$ | $R_3$ | $R_4$ | phys. data/$^1$H-NMR(60MHz, CDCl$_3$) |
|---|---|---|---|
| CH$_3$ | CH$_3$ | CH$_3$ | 3.30brs(2); 2.20s(3); 2.15s(3); 1.95s(3) |
| CH$_3$ | H | C$_6$H$_5$ | 7.6–7.1m(5); 6.70s(1); 3.25brs(2); 2.25s(3) |
| CH$_3$ | C$_3$H$_7$-i | C$_4$H$_9$-i | 3.55brs(2); 3.05hept(1); 2.50d(2)J=7, 2.10s(3); 1.9–1.6m(1); 1.25d(6)J=7; 0.90d(6)J=7 |
| i-C$_3$H$_7$ | H | C$_6$H$_5$ | 7.5–7.1m(5); 6.65s(1); 3.30brs(2); 3.00hept(1)J=7; 1.20d(6)J=7 |
| i-C$_3$H$_7$ | H | CH$_3$ | 6.15q(1)J=1; 3.15brs(2); 2.95hept(1)J=7; 2.30d(3)J=1; 1.20d(6)J=7 |
| i-C$_3$H$_7$ | CH$_3$ | CH$_3$ | 3.90brs(2); 3.00hept(1)J=7; 2.20s(3), 1.90s(3); 1.20d(6)J=7 |
| i-C$_3$H$_7$ | C$_3$H$_7$-i | H | 6.55s(1), 3.55brs(2); 3.05hept(1)J=7, 2.75hept(1)J=7; 1.25d(6)J=7; 1.20d(6)J=7 |
| C$_2$H$_5$ | C$_3$H$_7$-i | H | 6.65s(1), 2.73hept(1)J=7, 2.52q(2)J=7, 1.55bs(2), 1.28t(3)J=7, 1.25d(6)J=7 |

$$R_3\text{-}\underset{S}{\overset{}{\text{}}}\text{-}N=C=S,\ R_4,\ R_2 \tag{II}$$

| $R_2$ | $R_3$ | $R_4$ | phys. data/$^1$H-NMR(60MHz, CDCl$_3$) |
|---|---|---|---|
| H | H | C$_6$H$_5$ | 7.50–7.15m(5); 7.50d(1)J=1.5; 6.95d(1)J=1.5 |
| H | H | CH$_3$ | 6.85d(1)J=1; 6.60m(1); 2.40d(3)J=1 |
| H | CH$_3$ | CH$_3$ | 6.85s(1); 2.30s(3); 2.10s(3) |
| CH$_3$ | CH$_3$ | CH$_3$ | 2.30s(6); 2.10s(3) |
| CH$_3$ | H | C$_6$H$_5$ | 7.50–7.20m(5); 6.95s(1); 2.45s(3) |
| CH$_3$ | C$_3$H$_7$-i | C$_4$H$_9$-i | 3.05hept(1)J=7; 2.50d(2)J=7; 2.30s(3), 1.90–1.60m(1); 1.25d(6)J=7; 0.90d(6)J=7 |
| C$_3$H$_7$-i | H | C$_6$H$_5$ | 7.50–7.15m(5); 6.85s(1); 3.30hept(1)J=7; 1.30d(6)J=7 |
| C$_3$H$_7$-i | H | CH$_3$ | 6.45d(1)J=1; 3.25hept(1)J=7; 2.35brs(3); 1.30d(6)J=7 |
| C$_3$H$_7$-i | CH$_3$ | CH$_3$ | 3.25hept(1)J=7; 2.25s(3); 2.05s(3), 1.20d(6)J=7 |
| C$_3$H$_7$-i | C$_3$H$_7$-i | H | 6.60s(1), 3.35hept(1)J=7; 2.95hept(1)J=7; 1.30d(6)J=7; 1.25d(6)J=7 |
| C$_2$H$_5$ | C$_3$H$_7$-i | H | 6.68s(1), 2.94hept(1)J=7, 2.85q(2)J=7, 1.29t(3)J=7, 1.24d(6)J=7 |

EXAMPLE 2

Preparation of 1-tert.-butyl-3-(2,4-diisopropyl-3-thienyl)thiourea 5.75 g of the 2,4-diisopropylthienyl-3-isothiocyanate prepared according to Example 1 are diluted with 70 ml of toluene, and 2.16 g of tert.-butylamine are added dropwise with stirring. The reaction mixture is then further stirred for 2 hours at approximately +80° C., concentrated, and hexane is added to the residue. The resulting solid is filtered off, subsequently washed with hexane and finally purified by column chromatography on silica gel (eluant: ethyl acetate/hexane-1:3). The title compound of formula

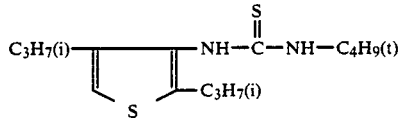

is obtained in the form of a colourless crystalline powder having a melting point of 168°–169° C. (compound No. 1.01).

The following thioureas of formula Ia according to the invention are prepared in an analogous manner.

$$R_3\text{-}\underset{S}{\overset{}{\text{}}}\text{-}NH\text{-}\overset{S}{\underset{}{\text{C}}}\text{-}NH\text{-}R_1,\ R_4,\ R_2 \tag{Ia}$$

| Compound No. | $R_1$ | $R_2$ | $R_3$ | $R_4$ | Smp. (°C.) |
|---|---|---|---|---|---|
| 1.02 | C$_3$H$_7$-i | H | H | C$_6$H$_5$ | 151–154 |
| 1.03 | C$_4$H$_9$-t | H | H | C$_6$H$_5$ | 130–133 |
| 1.04 | C(CH$_3$)$_2$C$_2$H$_5$ | H | H | C$_6$H$_5$ | 124–125 |
| 1.05 | C$_5$H$_9$-cyclo | H | H | C$_6$H$_5$ | 110–113 |
| 1.06 | C$_4$H$_9$-t | H | H | CH$_3$ | 102–105 |
| 1.07 | C$_4$H$_9$-t | H | CH$_3$ | CH$_3$ | 143–146 |
| 1.08 | C$_3$H$_7$-i | H | CH$_3$ | CH$_3$ | 120–122 |
| 1.09 | C$_4$H$_9$-t | CH$_3$ | CH$_3$ | CH$_3$ | 169–170 |
| 1.10 | C$_3$H$_7$-i | CH$_3$ | CH$_3$ | CH$_3$ | 125–126 |
| 1.11 | C$_4$H$_9$-t | CH$_3$ | H | C$_6$H$_5$ | 153–154 |
| 1.12 | C$_4$H$_9$-t | CH$_3$ | C$_3$H$_7$-i | C$_4$H$_9$-i | 87–90 |
| 1.13 | C$_3$H$_7$-i | CH$_3$ | C$_3$H$_7$-i | C$_4$H$_9$-i | 93–95 |
| 1.14 | C$_4$H$_9$-t | C$_3$H$_7$-i | H | C$_6$H$_5$ • | 157–158 |
| 1.15 | C$_3$H$_7$-i | C$_3$H$_7$-i | H | C$_6$H$_5$ | 155–156 |
| 1.16 | C$_4$H$_9$-t | C$_3$H$_7$-i | H | CH$_3$ | 122–123 |
| 1.17 | C$_3$H$_7$-i | C$_3$H$_7$-i | H | CH$_3$ | 125–127 |
| 1.18 | C$_4$H$_9$-t | C$_3$H$_7$-i | CH$_3$ | CH$_3$ | 95–96 |
| 1.19 | C$_3$H$_7$-i | C$_3$H$_7$-i | CH$_3$ | CH$_3$ | 101–103 |
| 1.20 | C$_3$H$_7$-i | C$_3$H$_7$-i | C$_3$H$_7$-i | H | 171–172 |
| 1.21 | C$_4$H$_9$-t | C$_2$H$_5$ | C$_3$H$_7$-i | H | 92–94 |

Also the following compounds of formula Ia can be prepared as indicated above.

| R1 | R2 | R3 | R4 |
|---|---|---|---|
| $C(CH_3)_2-C_2H_5$ | $C_3H_7$-i | $C_3H_7$-i | H |
| $C_5H_9$-cyclo | $C_3H_7$-i | $C_3H_7$-i | H |
| $C_3H_7$-i | $C_2H_5$ | $C_3H_7$-i | H |

| R1 | R2 | R3 | R4 |
|---|---|---|---|
| $C(CH_3)_2-C_2H_5$ | $C_3H_7$-i | $C_3H_7$-i | H |
| $C_5H_9$-cyclo | $C_3H_7$-i | $C_3H_7$-i | H |
| $C_3H_7$-i | $C_2H_5$ | $C_3H_7$-i | H |

EXAMPLE 3

Preparation of
1-tert.-butyl-3-(2,4-diisopropyl-3-thienyl)-S-methylisothiourea 1.65 g of methyl iodide are added at room temperature to 1.50 g of the 1-tert.-butyl-3-(2,4-diisopropyl-1-3-thienyl)thiourea obtained in accordance with Example 2 in 30 ml of ethanol. The mixture is heated for 5 hours at $+75°$ C. The mixture is then concentrated by evaporation and the residue is taken up in dichloromethane and washed twice with dilute sodium hydrogen carbonate solution. The separated organic phase is dried over magnesium sulfate and the solvent is evaporated off. The crude product is purified by column chromatography on silica gel (eluant: ethyl acetate/hexane-1:10). In this manner the title compound of formula

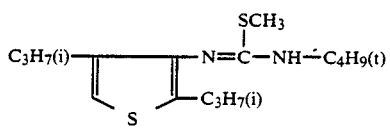

is obtained in the form of a colourless, viscous oil, $n_D^{22}=1.5404$ (compound No. 2.01).

The following isothioureas of formula Ib according to the invention are also prepared in an analogous manner:

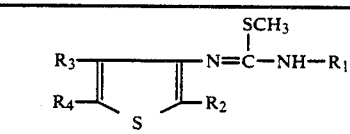

| Compound No. | R1 | R2 | R3 | R4 | Phys. data |
|---|---|---|---|---|---|
| 2.02 | $C_3H_7$-i | H | H | $C_6H_5$ | $n_D^{22} = 1.6445$ |
| 2.03 | $C_4H_9$-t | H | H | $C_6H_5$ | m.p. 51–54° C. |
| 2.04 | $C(CH_3)_2C_2H_5$ | H | H | $C_6H_5$ | $n_D^{23} = 1.6205$ |
| 2.05 | $C_5H_9$-cyclo | H | H | $C_6H_5$ | $n_D^{23} = 1.6480$ |
| 2.06 | $C_4H_9$-t | H | H | $CH_3$ | |
| 2.07 | $C_4H_9$-t | H | $CH_3$ | $CH_3$ | $n_D^{24} = 1.5665$ |
| 2.08 | $C_3H_7$-i | H | $CH_3$ | $CH_3$ | m.p. 50–53° C. |
| 2.09 | $C_4H_9$-t | $CH_3$ | $CH_3$ | $CH_3$ | $n_D^{23} = 1.5520$ |
| 2.10 | $C_3H_7$-i | $CH_3$ | $CH_3$ | $CH_3$ | $n_D^{23} = 1.5625$ |
| 2.11 | $C_4H_9$-t | $CH_3$ | H | $C_6H_5$ | |
| 2.12 | $C_4H_9$-t | $CH_3$ | $C_3H_7$-i | $C_4H_9$-i | $N_D^{25} = 1.5378$ |
| 2.13 | $C_3H_7$-i | $CH_3$ | $C_3H_7$-i | $C_4H_9$-i | $n_D^{25} = 1.5380$ |
| 2.14 | $C_4H_9$-t | $C_3H_7$-i | H | $C_6H_5$ | $n_D^{23} = 1.6045$ |
| 2.15 | $C_3H_7$-i | $C_3H_7$-i | H | $C_6H_5$ | m.p. 83–86° C. |
| 2.16 | $C_4H_9$-t | $C_3H_7$-i | H | $CH_3$ | $n_D^{23} = 1.5495$ |
| 2.17 | $C_3H_7$-i | $C_3H_7$-i | H | $CH_3$ | $n_D^{23} = 1.5555$ |
| 2.18 | $C_4H_9$-t | $C_3H_7$-i | $CH_3$ | $CH_3$ | m.p. 63–66° C. |
| 2.19 | $C_3H_7$-i | $C_3H_7$-i | $CH_3$ | $CH_3$ | $n_D^{25} = 1.5470$ |
| 2.20 | $C_4H_9$-t | $C_2H_5$ | $C_3H_7$-i | H | $n_D^{20} = 1.5312$ |
| 2.21 | $C_3H_7$-i | $C_3H_7$-i | $C_3H_7$i | H | $n_D^{23} = 1.5421$ |

Also the following compounds of formula Ib can be prepared as indicated above:

EXAMPLE 4

Preparation of the oxalic acid salt of
1-tert.-butyl-3-(2-isopropyl-5-methyl-3-thienyl)-S-methylisothiourea 3.5 ml of a saturated oxalic acid solution in ether are added, with stirring, to 0.85 g of the 1-tert.-butyl-3-(2-isopropyl-5-methyl-3-thienyl)-S-methylisothiourea obtained according to Example 3 dissolved in 1 ml of ether (diethyl ether). After dilution with 10 ml of ether, the mixture is further stirred for 15 minutes at room temperature. The resulting solid is filtered off with suction and then washed thoroughly three times with 10 ml of ether. The title compound is in the form of a colourless crystalline powder. m.p. 138°–140° C. (compound No. 3.01).

The following isothiourea salts of formula Ic according to the invention are prepared in an analogous manner:

$$\left[ R_3 \underset{R_4}{\overset{}{\diagdown}} \underset{S}{\overset{}{\diagup}} \overset{SR_5}{\underset{R_2}{\diagdown}} N=\overset{|}{C}-NH-R_1 \right] \cdot HY \quad (Ic)$$

| Comp. No. | R1 | R2 | R3 | R4 | R5 | Y | m.p. (°C.) |
|---|---|---|---|---|---|---|---|
| 3.02 | $C_3H_7$-i | $C_3H_7$-i | H | $C_6H_5$ | $CH_3$ | $H(COO)_2$ | 200–202 |
| 3.03 | $C_3H_7$-i | $CH_3$ | $CH_3$ | $CH_3$ | $CH_3$ | $H(COO)_2$ | 175–178 |
| 3.04 | $C_4H_9$-t | $CH_3$ | $CH_3$ | $CH_3$ | $CH_3$ | $H(COO)_2$ | 110–112 |

Also the following salts of formula Ic can be prepared in an analogous manner:

| R1 | R2 | R3 | R4 | R5 | Y |
|---|---|---|---|---|---|
| $C_4H_9$-t | $C_3H_7$-i | $C_3H_7$-i | H | $CH_3$ | $H(COO)_2$ |
| $C_3H_7$-i | $C_3H_7$-i | $CH_3$ | $CH_3$ | $CH_3$ | $H(COO)_2$ |
| $C_4H_9$-t | $C_2H_5$ | $C_3H_7$-i | H | $CH_3$ | $H(COO)_2$ |

EXAMPLE 5

Preparation of
1-tert.-butyl-3-(2,4-diisopropyl-3-thienyl)-carbodiimide 2.50 g of the 1-tert.-butyl-3-(2,4-diisopropyl-3-thienyl)thiourea obtained according to Example 2 and 2.60 g of 2-chloro-1-methylpyridinium iodide are introduced into 25 ml of acetonitrile and, at room temperature, a solution of 1.90 g of triethylamine in 12 ml of acetonitrile is added. The reaction mixture is then stirred for 2 hours at approximately $+45°$ C. After evaporation of the solvent, the residue is taken up in hexane/water. The separated organic phase is dried over magnesium sulfate and the solvent is removed in vacuo. The crude product is purified by column chromatography on silica gel (eluant: ethyl acetate/hexane-1:20). The title compound of formula

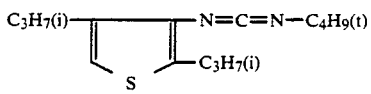

is obtained in the form of a colourless oil, $n_D^{23} = 1.5249$ (compound No. 4.01).

The following carbodiimides of formula Id according to the invention are prepared in an analogous manner:

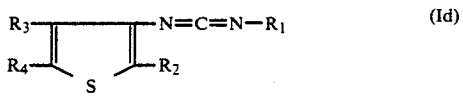
(Id)

| Compound No. | $R_1$ | $R_2$ | $R_3$ | $R_4$ | Phys. data |
|---|---|---|---|---|---|
| 4.02 | $C_3H_7$-i | H | H | $C_6H_5$ | $n_D^{23} = 1.6185$ |
| 4.03 | $C_4H_9$-t | H | H | $C_6H_5$ | $n_D^{23} = 1.6040$ |
| 4.04 | $C(CH_3)_2C_2H_5$ | H | H | $C_6H_5$ | $n_D^{24} = 1.5955$ |
| 4.05 | $C_5H_9$-cyclo | H | H | $C_6H_5$ | wax-like mass |
| 4.06 | $C_4H_9$-t | H | $CH_3$ | $CH_3$ | $n_D^{24} = 1.5360$ |
| 4.07 | $C_4H_9$-t | $CH_3$ | $CH_3$ | $CH_3$ | $n_D^{24} = 1.5335$ |
| 4.08 | $C_3H_7$-i | $CH_3$ | $CH_3$ | $CH_3$ | $n_D^{24} = 1.5375$ |
| 4.09 | $C_4H_9$-t | $CH_3$ | $C_3H_7$-i | $C_4H_9$-i | $n_D^{25} = 1.5215$ |
| 4.10 | $C_4H_9$-t | $CH_3$ | $C_3H_7$-i | $C_4H_9$-i | $n_D^{25} = 1.5323$ |
| 4.11 | $C_4H_9$-t | $C_3H_7$-i | H | $C_6H_5$ | $n_D^{23} = 1.5875$ |
| 4.12 | $C_3H_7$-i | $C_3H_7$-i | H | $C_6H_5$ | $n_D^{23} = 1.5985$ |
| 4.13 | $C_4H_9$-t | $C_3H_7$-i | H | $CH_3$ | $n_D^{23} = 1.5235$ |
| 4.14 | $C_3H_7$-i | $C_3H_7$-i | H | $CH_3$ | $n_D^{23} = 1.5285$ |
| 4.15 | $C_4H_9$-t | $C_3H_7$-i | $CH_3$ | $CH_3$ | $n_D^{24} = 1.5265$ |
| 4.16 | $C_3H_7$-i | $C_3H_7$-i | $CH_3$ | $CH_3$ | $n_D^{24} = 1.5335$ |
| 4.17 | $C_4H_9$-t | $C_2H_5$ | $C_3H_7$-i | H | $n_D^{20} = 1.5490$ |
| 4.18 | $C_3H_7$-i | $C_3H_7$-i | $C_3H_7$-i | H | $n_D^{23} = 1.5309$ |

Also the following compounds of formula Id can be prepared as indicated above:

| $R_1$ | $R_2$ | $R_3$ | $R_4$ |
|---|---|---|---|
| $C(CH_3)_2$—$C_2H_5$ | i-$C_3H_7$ | $C_3H_7$-i | H |
| $C_5H_9$-cyclo | i-$C_3H_7$ | $C_3H_7$-i | H |
| $C_3H_7$-i | $C_2H_5$ | $C_3H_7$-i | H |
| $C_4H_9$-t | H | H | $CH_3$ |
| $C_3H_7$-i | H | $CH_3$ | $CH_3$ |
| $C_4H_9$-t | $CH_3$ | H | $C_6H_5$ |

EXAMPLE 6

Formulations of active ingredients of formula I according to Preparation Examples 2 to 5 (throughout, percentages are by weight)

| Example 6.1: Emulsifiable concentrates | a) | b) | c) |
|---|---|---|---|
| active ingredient (comp. No. 1.01–1.21; 2.01–2.21; 3.01–3.04; 4.01–4.18) | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| Example 6.2: Solutions | a) | b) | c) | d) |
|---|---|---|---|---|
| active ingredient (comp. No. 1.01–1.21; 2.01–2.21; 3.01–3.04; 4.01–4.18) | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| Example 6.3: Granulates | a) | b) |
|---|---|---|
| active ingredient (comp. No. 1.01–1.21; 2.01–2.21; 3.01–3.04; 4.01–4.18) | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| Example 6.4: Dusts | a) | b) |
|---|---|---|
| Active ingredient (comp. No. 1.01–1.21; 2.01–2.21; 3.01–3.04; 4.01–4.18) | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| Example 6.5: Wettable powders | a) | b) | c) |
|---|---|---|---|
| Active ingredient (comp. No. 1.01–1.21; 2.01–2.21; 3.01–3.04; 4.01–4.18) | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| high dispersed silicic acid | 5% | 10% | 10% |
| kaolin | 62% | 27% | — |

The active ingredient or active ingredient combination is mixed with the adjuvants and the mixture is thoroughly ground in a suitable mill, affording wettable powders which can be diluted with water to give suspensions of the desired concentration.

| Example 6.6: Emulsifiable concentrate | |
|---|---|
| Active ingredient (comp. No. 1.01–1.21; 2.01–2.21; 3.01–3.04; 4.01–4.18) | 10% |
| octylphenol polyethylene glycol ether (4–5 moles of ethylene oxide) | 3% |
| calcium dodecylbenzenesulfoante | 3% |
| castor oil polyethylene glycol ether (36 moles of ethylene oxide) | 4% |
| cyclohexanone | 30% |
| xylene mixture | 50% |

Emulsions of any desired concentration can be produced from this concentrate by dilution with water.

| Example 6.7: Dusts | a) | b) |
|---|---|---|
| Active ingredient (comp. No. 1.01–1.21; 2.01–2.21; 3.01–3.04; 4.01–4.18) | 5% | 8% |
| talcum | 95% | — |
| kaolin | — | 92% |

Ready-for-use dusts are obtained by mixing the active ingredient with the carrier and grinding the mixture in a suitable mill.

| Example 6.8: Extruder granulate | |
|---|---|
| Active ingredient (comp. No. 1.01–1.21; 2.01–2.21; 3.01–3.04; 4.01–4.18) | 10% |
| sodium lignosulfonate | 2% |
| carboxymethylcellulose | 1% |
| kaolin | 87% |

The active ingredient or active ingredient combination is mixed and ground with the adjuvants, and the mixture is subsequently moistened with water. The mixture is extruded, granulated and then dried in a stream of air.

| Example 6.9: Coated granulate | |
|---|---|
| Active ingredient (comp. No. 1.01–1.21; 2.01–2.21; 3.01–3.04; 4.01–4.18) | 3% |
| polyethylene glycol (mol. wt. 200) | 3% |
| kaolin | 94% |

The finely ground active ingredient or active ingredient combination is uniformly applied, in a mixer, to the kaolin moistened with polyethylene glycol. Non-dusty coated granulates are obtained in this manner.

| Example 6.10: Suspension concentrate | |
|---|---|
| Active ingredient (comp. No. 1.01–1.21; 2.01–2.21; 3.01–3.04; 4.01–4.18) | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or active ingredient combination is intimately mixed with the adjuvants, giving a suspension concentrate from which suspensions of any desired concentration can be obtained by dilution with water.

EXAMPLE 7

Action against Boophilus microplus

Well-nourished female ticks are affixed to a PVC plate and covered with a cottonwood swab. For the treatment, 10 ml of an aqueous test solution containing 400 ppm of the test compound are poured over the test organisms. The cottonwool swab is then removed and the ticks are incubated for 4 weeks for oviposition. The activity against Boophilus microplus is demonstrated by death or sterility of the females or, in the case of eggs, by ovicidal action.

Compounds of formula I according to Examples 2 to 5 exhibit a good activity against Boophilus microplus in this test. In particular, compounds Nos. 4.01, 4.11 and 4.13 are more than 80% effective.

EXAMPLE 8

Action against Nilaparvata lugens

Rice plants are treated with an aqueous emulsion spray formulation containing 400 ppm of the active ingredient. When the spray coating has dried, the rice plants are each populated with cicada larvae in the $L_2$ and $L_3$ stage. The evaluation is carried out 21 days later. The percentage reduction in population (% effect) is ascertained by comparing the number of surviving cicadas on the treated plants with the number on the untreated plants.

Compounds of formula I according to Examples 2 to 5 exhibit a good activity against Nilaparvata lugens in this test. In particular, compounds Nos. 1.01, 1.14, 1.16, 1.18, 2.01, 2.14, 2.18, 4.01, 4.11 and 4.15 are more than 80% effective.

EXAMPLE 9

Action against Nephotettix cincticeps

Rice plants are treated with an aqueous emulsion spray formulation containing 400 ppm of the active ingredient. When the spray coating has dried, the rice plants are populated with cicada larvae in the $L_2$ and $L_3$ stage. The evaluation is carried out 21 days later. The percentage reduction in population (% effect) is ascertained by comparing the number of surviving cicadas on the treated plants with the number on the untreated plants.

Compounds of formula I according to Examples 2 to 5 exhibit a good activity against Nephotettix cincticeps in this test. In particular, compounds Nos. 1.01, 1.18, 2.01, 2.18 and 4.15 are more than 80% effective.

EXAMPLE 10

Action against Bemisia tabaci

Dward bean plants are placed in gauze cages and populated with Bemisia tabaci adults (whiteflies). After oviposition, all adults are removed and 10 days later the plants together with the nymphs are treated with an aqueous emulsion spray formulation of the test compounds (concentration 400 ppm). The evaluation, based on the hatching percentage compared with untreated control groups, is carried out 14 days after application of the test compound.

Compounds of formula I according to Examples 2 to 5 exhibit a good activity against Bemisia tabaci in this test. In particular, compounds Nos. 1.01 and 4.01 are more than 80% effective.

EXAMPLE 11

Action against Diabroatica balteata larvae

Maize seedlings are sprayed with an aqueous emulsion spray formulation containing 400 ppm of the active ingredient. When the spray coating has dried, the maize seedlings are each populated with 10 larvae of Diabrotica balteata in the $L_2$ stage and placed in a plastics container. Evaluation is carried out six days later. The percentage reduction in population (% effect) is ascertained by comparing the number of dead larvae on the treated plants with the number of dead larvae on the untreated plants.

Compounds of formula I according to Examples 2 to 5 exhibit a good activity against Diabrotica balteata in

17 this test. Compounds Nos. 1.01, 1.09 and 4.01 are more than 80% effective. Compound 2.01 is 100% effective.

EXAMPLE 12

Action against *Tetranychus urticae*

Young bean plants are populated with a mixed population of *Tetranychus urticae* and sprayed 1 day later with an aqueous emulsion spray formulation containing 400 ppm of the active ingredient. The plants are then incubated for 6 days at 25° C. and subsequently evaluated. The percentage reduction in population (% effect) is ascertained by comparing the number of dead eggs, larvae and adults on the treated plants with that on the untreated plants.

Compounds of formula I according to Examples 2 to 5 exhibit a good activity against *Tetranychus urticae* in this test. In particular, compounds Nos. 1.01, 1.14, 1.15, 1.18, 4.01 and 4.04 are more than 80% effective.

EXAMPLE 13

Action against *Spodoptera littoralis* caterpillars

Young soybean plants are sprayed with an aqueous emulsion spray formulation containing 400 ppm of the active ingredient. When the spray coating has dried, the soybean plants are each populated with 10 caterpillars of *Spodoptera littoralis* in the $L_3$ stage and placed in a plastics container. The evaluation is carried out 3 days later. The percentage reduction in population and the percentage reduction in feeding damage (% effect) are ascertained by comparing the number of dead caterpillars and the feeding damage, respectively, on the treated and untreated plants.

Compounds of formula I according to Examples 2 to 5 exhibit a good activity against *Spodoptera littoralis* in this test. In particular, compounds Nos. 1.16, 1.18, 1.19, 2.04, 2.14 and 4.11 are more than 80% effective.

EXAMPLE 14

Action against *Aphis craccivora*

Pea seedlings are infested with *Aphis craccivora* and then sprayed with a spray formulation containing 400 ppm of the active ingredient and incubated at 20° C. The evaluations are carried out 3 and 6 days later. The percentage reduction in population (% effect) is ascertained by comparing the number of dead aphids on the treated plants with the number on the untreated plants.

Compounds of formula I according to Examples 2 to 5 exhibit a good activity against *Aphis craccivora* in this test. In particular, compounds Nos. 1.01, 4.01, 4.11 and 4.15 are more than 80% effective.

EXAMPLE 15

Action against *Tetranychus cinnabarinus* (OP-resistant)

24 hours before the test for acaricidal action, the primary leaves of *Phaseolus vulgaris* plants are infected with an infested piece of leaf from a mass culture of *Tetranychus cinnabarinus* (the resistance relates to the tolerance to diazinone).

The so-treated infested plants are sprayed to drip point with an aqueous preparation containing 400 ppm of the respective test compound. After 48 hours and again after 7 days imagines and larvae (all mobile stages) are evaluated under a stereoscopic microscope for living and dead specimens. During the test run the plants are kept in greenhouse compartments at 25° C.

Compounds of formula I according to Examples 2 to 5 exhibit a good activity against *Tetranychus cin-*

18

*nabarinus* in this test. For example, compounds Nos. 1.14, 1.18 and 4.01 are 80–100% effective.

EXAMPLE 16

Action against *Musca domestica*

50 g of freshly prepared CSMA nutrient substrate for maggots are charged into each of a number of beakers. A specific amount of an acetonic solution containing 1% by weight of the respective test compound is pipetted onto the nutrient substrate present in the beakers to give an active ingredient concentration of 800 ppm. The substrate is then thoroughly mixed and the acetone subsequently allowed to evaporate over a period of at least 20 hours.

Then 25 one-day-old maggots of *Musca domestica* are put into each of the beakers containing the treated substrate for testing with each active ingredient. After the maggots have pupated, the pupae are separated from the substrate by flushing them out with water and then deposited in containers closed with a perforated top.

Each batch of pupae flushed out is counted (toxic effect of the active ingredient on the maggot development). A count is then made after 10 days of the number of flies which have hatched out of the pupae.

Compounds of formula I according to Examples 2 to 5 exhibit a good activity in the above test.

EXAMPLE 17

Action against *Dermanyssus gallinae*

2 to 3 ml of a solution containing 10 ppm of active ingredient and approximately 200 mites at different stages of development are placed in a glass container open at the top. The container is then closed with a cottonwool swab, shaken for 10 minutes until the mites are completely wet, and then briefly inverted so that the remainder of the test solution can be absorbed by the swab. The mortality of the mites is ascertained 3 days later.

Compounds of formula I according to Examples 2 to 5 exhibit a good activity against *Dermanyssus galline.*

EXAMPLE 18

Action against *Blattella germanica*

An amount of a 0.1% solution of the active ingredient in acetone sufficient to provide an application rate of 1 g/m² is placed in a Petri dish of 10 cm diameter. When the solvent has evaporated, 10 *Blattella germanica* nymphs (final nymph stage) are added to the prepared dish and exposed for 2 hours to the action of the test compound. The nymphs are then narcotised with $CO_2$, placed in a fresh Petri dish and kept in the dark at 25° C. and about 70% humidity. After 48 hours, the insecticidal activity is ascertained by determining the mortality rate.

Compounds of formula I according to Examples 2 to 5 exhibit a good activity in this test.

What is claimed is:

1. A compound of formula I

in which $R_1$ is $C_1$–$C_{12}$alkyl, $C_1$–$C_1$alkyl substituted by a $C_3$–$C_6$cycloalkyl radical, $C_3$–$C_8$cycloalkyl, or $C_3$–$C_6$- cycloalkyl substituted by a $C_1$-$C_4$alkyl radical; $R_2$, $R_3$ and $R_4$ are each, independently of the others, hydrogen, $C_1$-$C_6$alkyl, phenyl, or phenyl substituted by from 1 to 3 radicals from the group halogen, $C_1$-$C_6$alkyl, $C_1$-$C_4$alkoxy and $C_1$-$C_6$haloalkyl having from 1 to 9 halogen atoms; Z is a group —NH—CS—NH—, —N=C(S$R_5$)—NH— or —N=C=N—; and $R_5$ is $C_1$-$C_6$alkyl or $C_3$-$C_5$alkenyl; with the proviso that at least one of the radicals $R_2$, $R_3$ and $R_4$ is other than hydrogen; and the salts of compounds of formula I in which Z is the group —N=C(S$R_5$)—NH—.

2. A compound according to claim 1, wherein at least two of the radicals $R_2$, $R_3$ and $R_4$ are other than hydrogen.

3. A compound according to claim 1, wherein $R_4$ is hydrogen.

4. A compound according to claim 1, wherein $R_1$ is $C_1$-$C_4$alkyl or $C_3$-$C_5$cycloalkyl.

5. A compound according to claim 4, wherein $R_1$ is $C_4H_9(t)$ or $C_3H_7(i)$.

6. A compound according to claim 1, wherein $R_2$ and $R_3$ are each, independently of the other, $C_2$-$C_5$alkyl.

7. A compound according to claim 1, wherein $R_2$ and/or $R_3$ are $C_3H_7(i)$.

8. A compound according to claim 1, wherein $R_5$ is methyl or ethyl.

9. A compound according to claim 7 of the formula

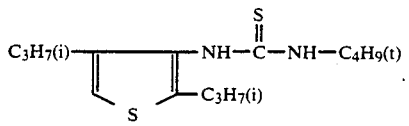

10. A compound according to claim 7 of the formula

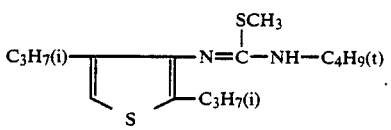

11. A compound according to claim 7 of the formula

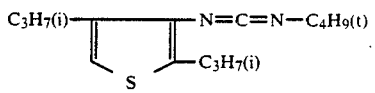

12. A compound according to claim 7 of the formula

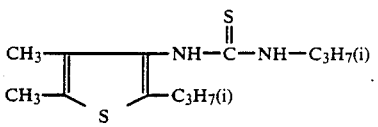

13. A compound according to claim 7 of the formula

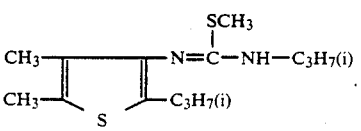

14. A compound according to claim 7 of the formula

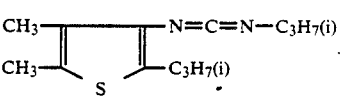

15. A compound of formula II

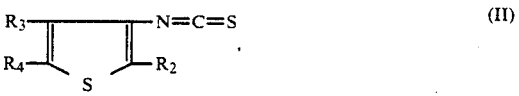

wherein $R_2$ to $R_4$ are as defined in claim 1.

16. A pesticidal composition that contains a compound according to claim 1 as active component together with suitable carriers and/or other adjuvants.

17. A method of controlling insects and representatives of the order Acarina, wherein the pests or their various stages of development, or the locus thereof, are treated or brought into contact with a pesticidally effective amount of a compound of formula I according to claim 1, or with a composition containing a pesticidally effective amount of that compound together with adjuvants and carriers.

18. A method according to claim 17 for controlling plant-destructive insects.

* * * * *